United States Patent [19]
Coll et al.

[11] Patent Number: 6,093,543
[45] Date of Patent: Jul. 25, 2000

[54] METHOD FOR DETECTING THE PRESENCE OF MALIGNANT CELLS USING A MULTI-PROTEIN DNA REPLICATION COMPLEX

[75] Inventors: Jennifer Coll, Baltimore; Linda H. Malkas; Robert J. Hickey, both of Abingdon, all of Md.

[73] Assignee: University of Maryland, Baltimore, Baltimore, Md.

[21] Appl. No.: 09/058,760

[22] Filed: Apr. 11, 1998

Related U.S. Application Data

[60] Provisional application No. 60/043,895, Apr. 11, 1997.

[51] Int. Cl.[7] ............................... C12Q 1/68; C12P 19/34
[52] U.S. Cl. ..................... 435/6; 435/91.5; 435/91.52; 435/91.1; 435/91.2
[58] Field of Search ............................ 435/6, 91.1, 91.2, 435/91.5, 91.52

[56] References Cited

U.S. PATENT DOCUMENTS 5,574,047  11/1996  Bumol .
5,616,461   4/1997  Schaeffer .

OTHER PUBLICATIONS

Azira et al, *Env. & Mol. Mutagenesis*, 27:30–33 (1996).
Mikita et al, *Biochemistry*, 27:4698–4705 (1988).
Murakami et al, *Proc. Natl. Acad. Sci., USA*, 83:6347–6351 (1986).
Sekowski et al, *Cancer Res.*, 58:3259–3263 (1998).
Bechtel et al, *Cancer Res.*, 58:3264–3269 (1998).
Coll et al, *Oncology Res.*, 9:629–639 (1997).
Sekowski, J.W., et al. "Mercuric Ion Inhibits the Activity and Fidelity of the Human Cell DNA Synthesome" *Toxicol. Appl. Pharmacol.* 145:268–276, 1997.
Coll, J.M., et al. "The Human Breast Cell DNA Synthesome: Its Purification from Tumor Tissue and Cell Culture" *Oncol. Res.* 8:435–447, 1996.
Malkas, L.H., et al. "A 21S Enzyme Complex from HeLa Cells That Functions in Simian Virus 40 DNA Replication in Vitro" *Biochemistry* 29:6362–6374, 1990.
Roberts, J.D., et al. "The fidelity of a human cell DNA replication complex" *Proc. Natl. Acad. Sci. USA* 85:7064–7068, 1988.

(List continued on next page.)

*Primary Examiner*—Kenneth R. Horlick
*Assistant Examiner*—Jeffrey Siew
*Attorney, Agent, or Firm*—Sughrue, Mion, Zinn, Macpeak & Seas, PLLC

[57] ABSTRACT

We describe herein the isolation and purification of a multi-protein complex for DNA replication from MDA MB-468 human breast cancer cells as well as human breast tumor tissue and xenografts from nude mice injected with human breast cancer cell line MCF-7. This complex, designated the "DNA synthesome", fully supports the in vitro replication of simian virus 40 (SV40) origin-containing DNA in the presence of the viral large T-antigen. Since the SV40 virus utilizes the host's cellular proteins for its own DNA replication, our results indicate that the DNA synthesome plays a role not only in viral DNA synthesis but in human breast cell DNA replication as well. Our studies demonstrate that the following DNA proteins are incorporated into the DNA synthesome: DNA polymerase $\alpha$, DNA primase, DNA polymerase $\delta$, proliferating cell nuclear antigen (PCNA), replication protein A (RP-A), replication protein C (RF-C), DNA topoisomerase I and II, and DNA polymerase $\epsilon$. Furthermore, our results obtained from a forward mutagenesis assay suggest that DNA isolated from a non-malignant breast cell line mediates SV40 DNA replication by an error-resistant mechanism whereas the DNA synthesome derived from malignant breast cells and tissue exhibited a lower fidelity for DNA synthesis in vitro. Overall, our data support the role of the DNA synthesome as mediating breast cell DNA replication in vitro and in vivo, with continued characterization of the DNA synthesome providing important insight into the molecular mechanisms regulating breast cancer call DNA replication.

23 Claims, 8 Drawing Sheets

OTHER PUBLICATIONS

Malkas, L.H., et al., "Sequence recognition protein for the 17–base–pair A+T–rich tract in the replication origin of simian virus 40 DNA" *Proc. Natl. Acad. Sci. USA* 86:70–74, 1989.

Hickey, R.J., "Multienzyme Complex for DNA Replication in HeLa Cells" In: Moses, R.E.; Summers, W.C., eds. *DNA Replication and Mutagenesis* Washington, D.C.; American Society for Microbiology; pp. 41–54, 1988.

Sekowski et al Proc. Annu. meet Am Assoc. Cancer Res. vol. 38 pp. A270, 1997.

Coll J. et al Proc. Annu. Meet Am. Assoc. Cancer Res. vol. 37 pp. 3409, 1997.

Lin S. et al Proc. Annu. Meet Am. Assoc. Cancer Res. vol. 37 pp A3413, 1997.

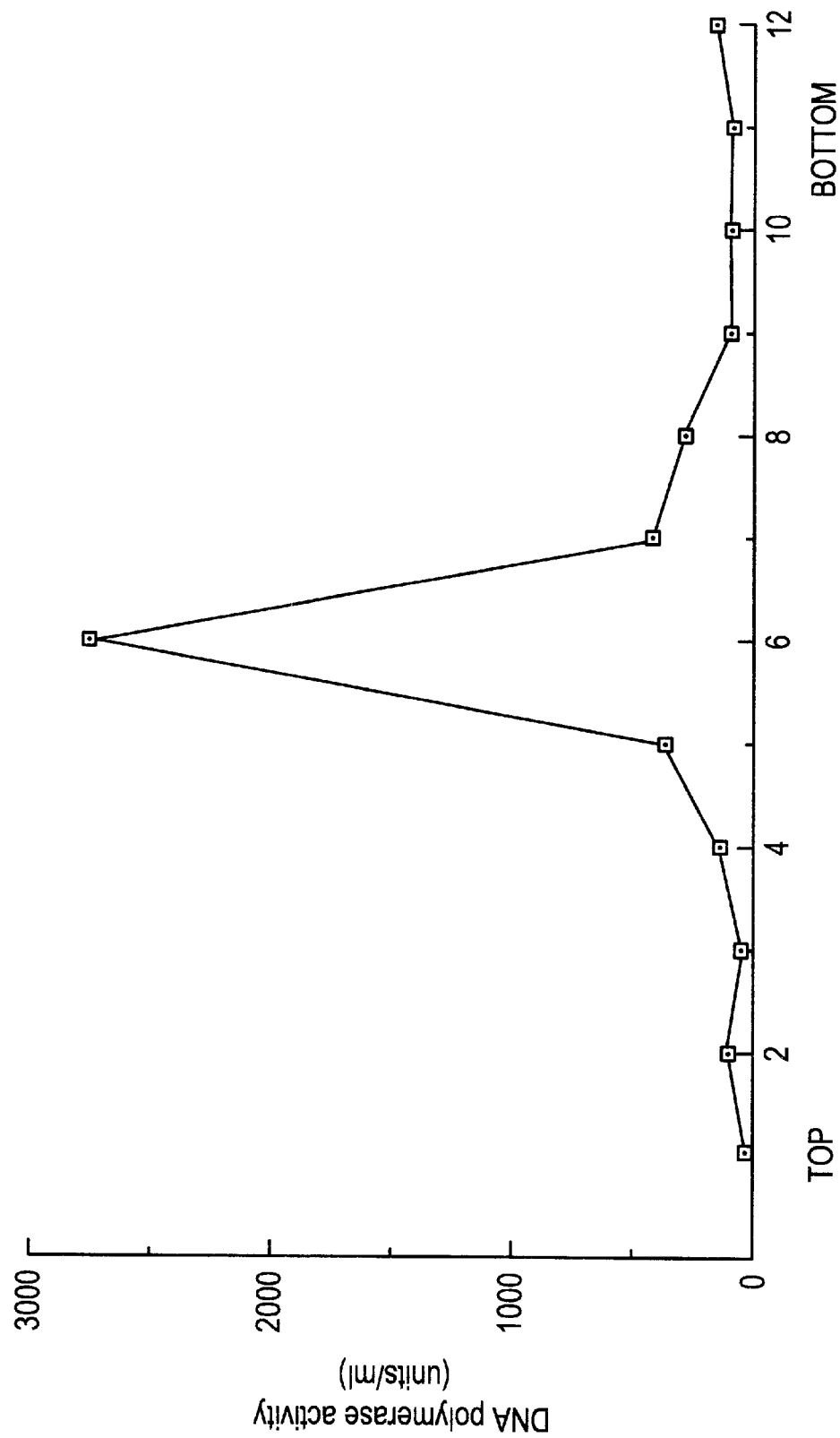

METHOD FOR DETECTING THE PRESENCE OF MALIGNANT CELLS USING A MULTI-PROTEIN DNA REPLICATION COMPLEX

CROSS-REFERENCE TO RELATED APPLICATIONS

This application is an application filed under 35 U.S.C. § 111(a) claiming benefit pursuant to 35 U.S.C. § 119(e)(1) of the filing date of Provisional Application No. 60/043,895, filed Apr. 11, 1997, pursuant to 35 U.S.C. § 111(b).

SPONSORSHIP

Support for the research disclosed herein was provided by the University of Maryland, Baltimore (Cancer Research Center Award); the University of Maryland School of Medicine (DRIF award); the U.S. Army Breast Cancer Research Program (Army Grant No. DAMD17-94-J4157) and the National Institutes of Health/National Cancer Institute (NIH/NCI Grant No CA65754 & CA57350).

FIELD OF THE INVENTION

The field of the invention generally relates to a method for isolating and purifying a multi-protein complex for DNA replication designated the "DNA synthesome". The field of the invention specifically relates to a mini-fractionation protocol designed to rapidly and efficiently isolate the intact DNA replication machinery from small quantities of cell culture or tissue samples. The field of the invention also relates to a method for correlating mutation frequency with malignancy using the DNA synthesome from cell or tissue samples.

BACKGROUND OF THE INVENTION

Breast cancer is one of the most commonly diagnosed female cancers and the second leading cause of cancer death among women [1]. Recently, numerous reports have underscored the important role of cell proliferation rate as a prognostic factor for breast carcinoma. Studies using flow cytometry to measure the DNA content of breast tumor cells show a strong association between a high S-phase fraction and poor prognosis for relapse-free survival in patients with lymph node negative breast cancer [2]. In addition to a high rate of DNA synthesis, mammary cancer cells exhibit extensive DNA damage [3], as compared to non-malignant breast cells. The increased mutation frequency that accompanies the cellular transformation process is postulated to arise from molecular alterations of specific DNA replication and/or repair proteins [4]. Despite the knowledge that a high proliferation activity and increased mutation frequency correlate with breast cancer progression, there is a paucity of information regarding the regulation and precise molecular mechanisms of human breast cell DNA replication.

To date, several mammalian enzymes and proteins have been shown to be required for DNA replication in vitro [5–10]. In particular, the proteins necessary to support SV40 based cell-free DNA synthesis include: DNA polymerase α, DNA primase, DNA polymerase δ, proliferating cell nuclear antigen (PCNA), replication protein A (RP-A), replication factor C (RF-C), and DNA topoisomerases I and II [11]. As mammalian cell DNA replication represents an intricate yet highly coordinated and efficient process, it follows that the proteins mediating DNA synthesis may be organized into a multiprotein complex. In support of this hypothesis, several reports have described the isolation of large macromolecular complexes of replication essential proteins from extracts of eukaryotic cells [9,11,12].

Our laboratory was the first to isolate and characterize a multiprotein DNA replication complex from human (HeLa) cells and murine (FM3A) mammary carcinoma cells that fully supports origin specific and large T-antigen dependent papovavirus DNA replication in vitro [13–15]. The multiprotein complex was observed to retain its ability to replicate papovavirus DNA after additional purification by anion-exchange chromatography and sucrose or glycerol gradient sedimentation [13–15]. In addition, the integrity of the multiprotein complex was maintained after treatment with salt, detergents, RNase, DNase and electrophoresis through native polyacrylamide gels [15,16]. These results suggest that the association of the proteins with one another is independent of non-specific interactions with other cellular macromolecules.

We report here, for the first time, that breast cancer cells also utilize a multiprotein complex to carry out cellular DNA synthesis, and we now designate this complex the DNA synthesome. We describe the isolation and purification of the DNA synthesome from MDA MB-468 human breast cancer cells and most importantly from human breast tumor cell xenografts, as well as from biopsied human breast tumor tissue. Furthermore, we discuss the results of a forward mutagenesis assay which establish that the DNA synthesome isolated from breast cancer cells and tissue has a lower fidelity for DNA replication than the DNA synthesome isolated from a normal breast cell line. Ultimately, we anticipate that the complete characterization of this DNA synthesome will lead to important new insights into understanding the molecular mechanisms of breast cancer cell DNA replication.

SUMMARY OF THE INVENTION

It is an object of the invention to provide an improved method for isolating and purifying the intact DNA replication machinery, the machinery comprising a multi-protein DNA replication complex capable of supporting SV40 DNA replication and designated herein as the "DNA synthesome".

It is a second object of the invention to facilitate the rapid and efficient isolation of the DNA synthesome from small quantities of cell culture or tissue samples or biopsies.

It is a third object of the invention to provide to a mini-fractionation protocol designed to rapidly and efficiently isolate the intact DNA synthesome from small quantities of cell culture or tissue samples. This protocol is a straightforward and easy-to-perform process that allows the purification of the DNA synthesome from cells or tissue within 48 hours using standard laboratory equipment.

It is a fourth object of the invention to use the mini-fractionation DNA protocol for DNA synthesome isolation and purification in all studies of the DNA synthesome, from toxicology screening work to anticancer drug development.

It is a final object of the invention to utilize the isolated, purified DNA synthesome from a cell or tissue sample to measure mutation frequency, said mutation frequency serving as a tool for detecting the presence of malignancy.

BRIEF DESCRIPTION OF THE DRAWINGS

FIG. 3: Depicts the velocity sedimentation analysis of the DNA synthesome present in MDA MB-468 Q-Sepharose peak fraction. 0.8 ml of the Q-Sepharose peak fraction were layered onto a 9 ml 10–30% sucrose gradient containing 0.5 KCl. Centrifugation and the assay for DNA polymerase activity were performed as described in the detailed description. One unit of activity denotes 1 nmol of TMP incorporated into DNA per hour at 35° C.

(FIG. 4B) RP-A; (FIG. 4C) RF-C; (FIG. 4D) PCNA and (FIG. 4E) DNA primase. Following incubation with the appropriate species-species secondary antibody conjugated to horseradish peroxidase, the immobilized proteins were detected using a light enhanced chemi-luminescence system (Amersham).

DETAILED DESCRIPTION OF THE INVENTION

Materials and Methods

Figure 1:
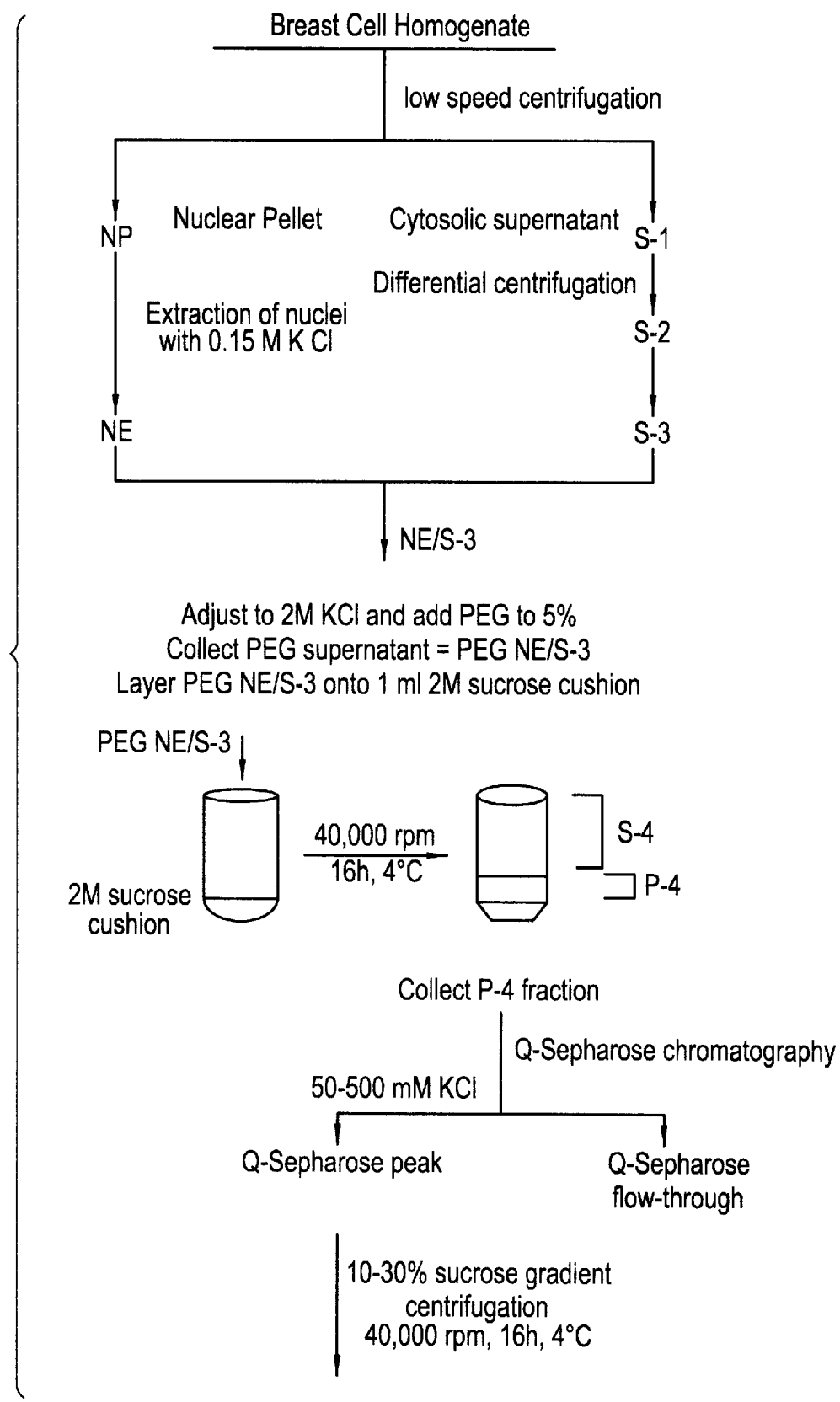
FIG. 1: Depicts a flow diagram of the isolation scheme used to purify the DNA synthesome from MDA MB-468 human breast cancer cells.

Materials. [α-$^{32}$P]dCTP (3000 Ci/mmol; 370 MBq/ml; 10 mCi/ml) and [$^3$H]thymidine (90 Ci/mmol; 37 MBq; 2.5 mCi/ml) were obtained from DuPont New England Nuclear (Boston, Mass.). Camptothecin was purchased from TopoGen, Inc. (Columbus, Ohio). The drug was dissolved in dimethyl sulfoxide and stored in aliquots at −20° C. Purified topoisomerase I enzyme (4 ng/ml) and a topoisomerase II assay kit were purchased from TopoGen, Inc. (Columbus, Ohio).

Cell Culture. Suspension cultures of MDA MB-468 human breast cells were adapted from monolayer cultures. The cells were grown in Joklik's modified Eagle's medium supplemented with 5% each of irradiated new-born calf serum and fetal bovine serum. Exponentially growing cells (5×10$^5$ cells/ml of medium) were harvested and washed three times with phosphate buffered saline (PBS): 20 mM Na$_2$HPO$_4$, 0.15 mM NaCl, 2.7 mM KCl, 1.5 mM KH$_2$PO$_4$. The cells were then pelleted by low-speed centrifugation (1000 rpm, 5 minutes, 4° C.), and the cell pellets stored at −80° C. until fractionation. Hs587Bst cells were cultured in monolayer in Dulbecco's Modified medium supplemented with 30 ng/ml of epidermal growth factor and 10% fetal bovine serum. Sub-confluent cells were harvested and washed three times with PBS. The cells were then pelleted by low-speed centrifugation (1000 rpm, 5 minutes, 4° C.) and the pellets stored at −80° C. until fractionation. MCF-7 cells were cultured in Eagle's minimum essential medium containing 5% fetal bovine serum and 600 µg/ml of neomycin sulfate, as described in Yue et al. [17]. Subconfluent MCF-7 cells were scraped into Hank's solution and centrifuged at 1000 rpm for 2 minutes at 4° C. The cells were then prepared for inoculation into intact nude mice according to published procedures [17].

Human Breast Tumor Tissue. A biopsy from an infiltrating ductal type carcinoma of the female mammary gland was immediately frozen at −80° C. after resection. In order to examine the tumor tissue for the presence of a functional DNA synthesome, the breast tumor tissue was thawed and subjected to the purification protocol described in a later section of these Materials and Methods.

Isolation and Purification of the DNA Synthesome from Breast Cancer Cells: Cell Fractionation. MDA MB-468 (20 g) and Hs587Bst (2 g) cells were homogenized and the breast cell DNA synthesome was purified according to our previously published, procedures [13–15] and as outlined in FIG. 1. Briefly, the respective cell pellet was resuspended in 2 volumes of buffer (50 mM Tris-HCl (pH 7.5), 0.25 M sucrose, 5 mM MgCl$_2$, 0.1 mM PMSF, 0.1 mM AAN (pH 7.5) and 1 mM DTT) and homogenized using a loose-fitting Dounce homogenizer. The homogenate was then fractionated into a nuclear pellet and cytosolic extract. The nuclei were extracted with a low salt buffer (0.15 M KCl) while the cytosolic fraction was used to prepare a post-microsomal supernatant (S-3). The nuclear extract and the post-microsomal supernatant were combined and, adjusted to 2M KCl and 5% (w/v) polyethylene glycol. The mixture was rocked for 1 h at 4° C., then centrifuged at 16,000 rpm for 15 minutes (4° C.). The resulting supernatant was then dialyzed against buffer A [13] containing 0.25 M sucrose. The dialyzed fraction was clarified by centrifugation at 16,000 rpm for 15 minutes and the supernatant solution, was layered onto a 1 ml 2 M sucrose cushion containing buffer A. After centrifugation at 40,000 rpm for 16 h (4° C.), the supernatant S-4 and sucrose interface P-4 fractions were collected and dialyzed against buffer B [13]. The fractions were then immediately tested for DNA polymerase α and in vitro SV40 DNA replication activities. Column Chromatography. 5 mls of the dialyzed MDA B-468 P-4 fraction were loaded onto a 1 ml Q-Sepharose (Pharmacia) column (1 cm³ bed volume/25 mg protein) pre-equilibrated with buffer B. The protein not binding to the matrix was collected and designated the column flow-through. After washing the matrix with 8 column volumes of buffer B, the column was eluted with 10 volumes of a linear 50–500 mM gradient of KCl. Fractions of 0.5 ml were collected and assayed for protein and enzymatic activity. Fractions containing the peak of DNA polymerase α and in vitro SV40 DNA replication activities were pooled, dialyzed against TDEG buffer [13] and stored at −80° C.

Velocity Sedimentation Analysis of the DNA Synthesome Isolated from MDA MB-468 Breast Cancer Cells. 0.6 ml (600 μg of protein) of the DNA synthesome present in the Q-Sepharose peak fraction was layered over a 10 ml 10–30% sucrose gradient containing 0.5 M KCl. Velocity sedimentation analysis was performed as described in a previously published report from this laboratory [15]. The sedimentation analysis of marker proteins (horse spleen apoferritin (17S) and yeast alcohol dehydrogenase (7S), was performed on parallel gradients to verify that the gradient was isokinetic.

Micro-isolation and Purification of the DNA Synthesome from Breast Tumor Tissue: Cell Fractionation. The DNA synthesome was purified from breast cancer tissue according to a modified version of the isolation scheme depicted in FIG. 1 and as described in a previous section of these methods. All steps of the fractionation process were altered to facilitate the purification of the DNA synthesome from small quantities of breast tumor tissue. The human breast tumor (8.55 g) was dissected and finely chopped with a tissue chopper at 4° C. The minced breast tissue was then suspended in 1 volume of buffer (50 mM Tris-HCl (pH 7.5), 0.25 M sucrose, 5 mM $MgCl_2$, 0.1 mM PMSF, 0.1 mM AAN (pH 7.5) and 1 mM DTT) and homogenized using a 1 ml Dounce homogenizer. The homogenate was centrifuged at 2,000 rpm for 10 minutes (4° C.), and the crude nuclear pellet (NP) and cytosolic fraction (S-1) were collected separately. The nuclear pellet was resuspended in 1 volume of nuclei extraction buffer [13] containing 0.15 M KCl. After rocking the nuclear pellet for 2 h at 4° C., the extracted nuclei were centrifuged at 22,300 rpm for 2.1 minutes (4° C.) using a TLA 100.3 rotor and the supernatant (NE) retained. In order to remove mitochondria and microsomes, the S-1 fraction was subjected to differential centrifugation using a TLA 100.3 rotor: 17,800 rpm, 3.2 minutes and 59,700 rpm, 22.2 minutes, respectively. The final post-microsomal supernatant (S-3) was collected. The NE was combined with the S-3 fraction; 4.5 mLs of the NE/S-3 fraction were then layered over a 0.5 ml 2 M sucrose cushion. After centrifugation at 40,000 rpm for 16 h (4° C.) using a Beckman SW55.Ti swinging bucket rotor, the S-4 and P-4 fractions were collected, dialyzed against a low-salt TDEG buffer, and assayed for their respective enzymatic activities. These same steps were followed to purify the DNA synthesome from the xenografts grown in nude mice. Column Chromatography. 0.7 mls of the dialyzed human breast tumor P-4 fraction (3.3 mg protein) were loaded onto a 0.15 ml DE52 cellulose column, pre-equilibrated in TDEG buffer containing 5 mM KCl. The protein not binding to the matrix was collected, and designated the column flow-through. The column was washed with 8 column volumes of pre-equilibration buffer. Matrix-bound protein was then eluted with 8 volumes of TDEG buffer containing 1M KCl. Fractions of approximately 0.1 ml were collected, dialyzed against TDEG buffer, and assayed for their DNA polymerase α and in vitro DNA replication activities.

Purification of SV40 Large T-antigen. SV40 large T-antigen was purified from 293 cells infected with a recombinant adenovirus vector, Ad-SVR284, as detailed elsewhere [18].

In vitro SV40 DNA Replication Assay. Assay reaction mixtures (12.5 μl) contained 80 mM Tris-HCl (pH 7.5); 7 mM $MgCl_2$; 1 mM DTT; 3–20 μg protein fraction; 0.5–1.0 μg purified SV40 large T-antigen; 25 ng plasmid pSVO⁺ [19] containing and insert of SV40 replication-origin DNA sequences; 100 μM each dTTP, dATP, dGT?; 200 μM each rCTP, RGTP, UTP; 4 mM ATP; 25 μM [α-$^{32}$P]dCTP; 40 mM creatine phosphate; 1 μg creatine kinase. Each reaction was incubated for 2 h at 35° C. The replication assay reaction products were processed using DE81 (Whatman) filter binding to quantitate the amount of radiolabel incorporated into the replication products [20]. One unit of SV40 replication activity is equivalent to the incorporation of 1 pmol of dNMP into SV40 replication-origin containing plasmid DNA per 2 h under these described assay conditions.

Enzyme Assays. DNA polymerase α activity with activated calf thymus DNA templates was assayed according to published procedures [21,22]. One unit of DNA polymerase α activity is equivalent to 1 nmol of total [³H]TMP incorporated into DNA per hour at 35° C. The assay for DNA topoisomerase I activity is a modification of published methods [19] and is described in detail by Hickey et al. [23]. DNA topoisomerase II activity was measured using an assay kit purchased from TopoGen, Inc.

Immunodetection of DNA Polymerases δ, ε, RP-A, RF-C, PCNA and DNA Primase. Denaturing polyacrylamide gel electrophoresis of the various protein fractions was performed as previously described [24]. The resolved polypeptides were transferred (15 volts, 16 h, 4° C.) to nitrocellulose membranes, and immunodetection of the respective DNA replication proteins was performed using a light-enhanced chemiluminescence system (Amersham). A monoclonal antibody prepared against the C-terminal portion of DNA polymerase δ was used at a 1:100 dilution to probe membranes for the 125 kD polymerase δ polypeptide. The anti-polymerase ε antibody which recognizes the 140 and, >200 kD forms of polymerase ε, was used at a 1:1000 dilution. Both the anti-RF-C monoclonal antibody (mAb-11), which recognizes the 140 kD subunit of the RF-C protein-complex, and the anti-RP-A antibody (p34-20), which recognizes the 34 kD subunit of RP-A, were generous gifts from Dr. Bruce Stillman. Both antibodies were used. at a 1:500 dilution. The anti-DNA primase antibody, a gift from Dr. William Copeland, was used at a 1:500 dilution. The anti-PCNA antibody was used at a dilution of 1:1000. The appropriate species-specific horseradish peroxidase conjugated secondary antibodies, were used in the immunoblots at a dilution of 1:5000.

Forward Mutagenesis Assay: Transfection and Plating. 12 ng of pBK-CMV plasmid DNA (Stratagene), encoding the lac-Zα gene, were incubated with 15–20 μg of protein fraction per in vitro DNA replication assay. The replicated pBK-CMV DNA was then Dpn I digested, precipitated as described [20] and used in the transfection of E. coli strain XL1-Blue MRF'. Bacterial stocks maintained in Luria broth, containing 10% glycerol, were mixed with 300 μg of the pBK-CMV DNA replicated in vitro and this mixture was incubated for 10 minutes on ice; subsequently, the DNA was electroporated into the cells under the following conditions:

1.4 kV, 25 µF, 200 ohms. Immediately following electroporation, 960 µls of chilled, sterile SOC buffer (20 mM glucose in Luria broth media) were added to the reaction cuvette. The electroporated mixture was then incubated in a rotary shaker (250 rpm) at 35° C. for 1 h. An aliquot of the incubated culture, sufficient to yield 100–600 bacterial colonies per plate, was spread on top of 20 mls of solidified Luria broth agar containing 0.5 mg/ml kanamycin, 25 mg/ml IPTG and 25 mg/ml X-gal. (These plating conditions yield an intense blue colored bacterial colony when the bacteria express the unmutated plasmid and a light blue to white colored bacterial colony when the bacteria contain plasmids harboring mutations in the lac-Zα gene.)

Scoring of Mutant Phenotypes. Mutant phenotypes, resulting from the inactivation of the lac-Zα gene in the pBK-CMV plasmid, were scored after approximately 12–15 hours of incubation at 35° C. In order to reproducibly score the variable color intensities of the mutant phenotypes, a scale of blue color intensities has been established [25]. Unmutated. pBK-CMV DNA generates a dark blue color which, on a scale of 0–4, is assigned a value of 4. The variable mutant phenotypes are distinguished as $0^+$ (white/colorless), $1^+$ (faint blue), $2^+$ (medium blue) and $3^+$ (almost wild type). In order to eliminate false positives resulting from plating artifacts, mutant colonies were picked from the plates, diluted in 50 mM sodium borate buffer (pH 9.0) and mixed with an equal dilution of bacteria containing unreplicated pBK-CMV plasmid. Plating of this mixture on the agar plates containing the color substrate X-gal (see above) enhances the contrast between the wild-type and mutant phenotypes as well as permits the scoring of subtle phenotypic differences arising from small variations in the position and number of point mutations within the lac-Zα gene.

Results

Human Breast Cancer Cell DNA Replication Proteins Co-fractionate as a Readily Sedimentable Form In order to determine whether a sedimentable complex of DNA replication proteins could be isolated from human breast cancer cells, as previously demonstrated for HeLa [13,14] and FM3A cells [15], we subjected MDA MB-468 cells to the fractionation scheme outlined in FIG. 1. The PEG NE/S-3, S-4 and P-4 fractions were collected and assayed for DNA polymerase α activity. The majority of the enzyme's activity partitioned with the sedimentable P-4 fraction following polyethylene glycol precipitation and discontinuous gradient centrifugation of the NE/S-3 fraction (Table 1). This result is consistent with our earlier work on the purification of the DNA synthesome from HeLa and FM3A cells [13–15], in which the DNA polymerase a activity contained in the DNA synthesome partitioned to the P-4 fraction at the sucrose interface.

In addition to determining DNA polymerase α activity, we assayed the PEG NE/S-3, S-4 and P-4 fractions for in vitro SV40 DNA replication activity (Materials and Methods). DE81 filter binding analysis was used to quantitate the level of [α-$^{32}$P]dCMP incorporation into SV40 DNA replication products. Following subfractionation of the PEG NE/S-3 fraction into the S-4 and P-4 fractions, the ability to support SV40 DNA replication in vitro partitioned exclusively with the sedimentable P-4 fraction (Table 1). This pattern of partitioning of DNA replication activity, is also consistent with our earlier work on the purification of the synthesome from HeLa and FM3A cells [13–15]. Only negligible amounts of radiolabel were incorporated into DNA replication products when reactions lacked SV40 large T-antigen. These data indicate that all of the activities required to execute large T-antigen dependent SV40 DNA replication reside in the human breast cancer cell sedimentable P-4 fraction.

TABLE 1

DNA polymerase α and in vitro DNA replication activities fractionate with the P-4 fraction.

| FRACTION | PEG NE/S-3 | S-4 | P-4 |
|---|---|---|---|
| DNA Polymerase α* | 132.5 | 0.3 | 188.3 |
| DNA Replication (+T)# | 103.8 | 8.8 | 110.6 |
| DNA Replication (−T)# | 3.1 | 0.0 | 0.2 |

*DNA polymerase activity with activated calf thymus DNA templates was assayed according to published procedures (21, 22). One unit of DNA polymerase activity equals 1 nmole of [$^3$H]-TMP incorporated into DNA per hour at 35° C. These values represent the average of three experiments.
In vitro SV40 DNA replication assays were performed as described in the Materials and Methods. One unit of SV40 replication activity is equal to the incorporation of 1 pmole of [$^{32}$P]-dCMP into SV40 origin containing DNA per 2 hours at 35° C. These values represent the average of three experiments.

Further Purification of the Human Breast Cancer Cell DNA Synthesome

Figure 2:
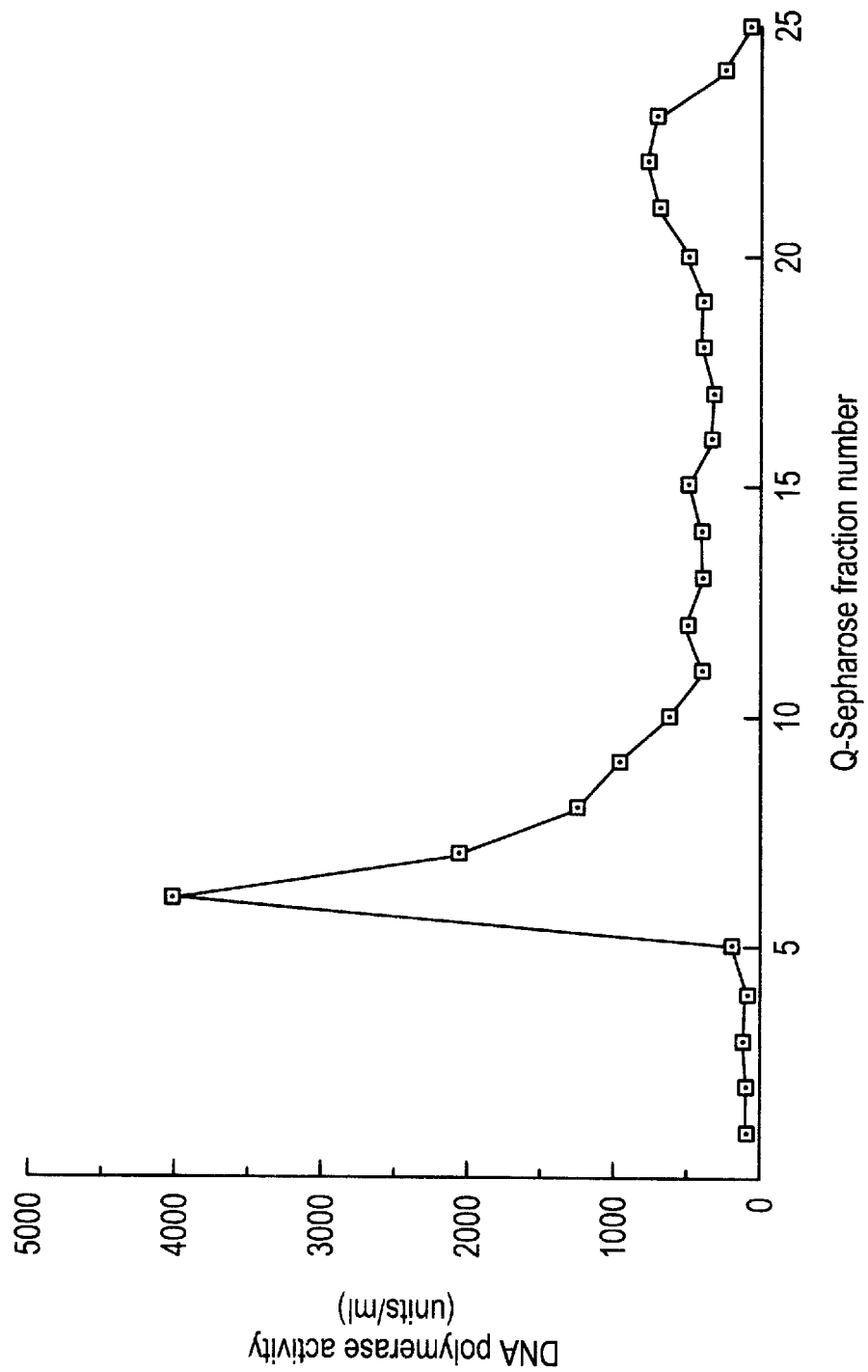
FIG. 2: Depicts the Q-Sepharose chromatographic profile of DNA polymerase α activity in the MDA MB-468 derived P-4 fraction.

We further purified the breast cancer cell DNA synthesome from the sedimentable P-4 fraction by Q-Sepharose anion-exchange chromatography; a method successfully employed for the purification of the DNA synthesome from HeLa cells [13,14]. The P-4 fraction was applied to a 1 ml Q-Sepharose column and the DNA synthesome eluted by a linear gradient of KCl (50–500 mM). FIG. 2 shows the profile of DNA polymerase α activity as it eluted from the Q-Sepharose column. The DNA polymerase α activity eluted from the column as an initial sharp peak at lower salt concentrations (fractions 6–10), with an additional small peak of activity at higher salt concentrations (fractions 21–23). Negligible amounts of enzyme activity were found in the column flow-through and wash fractions (data not shown).

The peak of DNA polymerase α activity that eluted from the Q-Sepharose column (fractions 6–10), was designated the Q-Sepharose peak. Both the peak and the column flow-through fractions were assayed for in vitro SV40 DNA replication activity. The Q-Sepharose peak contained over 80% of the large T-antigen dependent in vitro DNA replication activity; while the column flow-through fraction supported significantly less DNA synthesis (Table 2).

TABLE 2

In vitro DNA replication activities fractionate with the P-4 fraction.

| FRACTION | Q-Sepharose Peak | Flow Through (FT) | Sucrose Gradient |
|---|---|---|---|
| DNA Replication (+T)# | 136.6 | 3.4 | 141.2 |
| DNA Replication (−T)# | 8.5 | 1.8 | 10.2 | in vitro SV40 DNA replication assays were performed as described in the Materials and Methods. One unit of SV40 replication activity is equal to the incorporation of 1 pmole of [$^{32}$P]dCMP into SV40 origin containing DNA per 2 hours at 35° C. These values represent the average of three experiments.

Velocity Sedimentation Analysis of the Breast Cancer Cell DNA Synthesome

We determined the sedimentation coefficient of the breast cancer cell DNA synthesome by subjecting the Q-Sepharose peak fraction to velocity sedimentation analysis in a 10–30% sucrose gradient containing 0.5M KCl [15]. The sucrose gradient fractions were collected and assayed for DNA polymerase α and in vitro SV40 DNA replication activities. Both activities co-sedimented in the sucrose gradient with a sedimentation coefficient of 18S (FIG. 3; Table 2). This 18S sedimentation coefficient for the breast cell DNA synthesome corresponds to the S-value obtained for the HeLa cell DNA synthesome. Presumably, the 18S value of the human breast cancer cell DNA synthesome accounts for its ready sedimentation to the sucrose interphase following the centrifugation of the PEG NE/S-3 fraction (FIG. 1).

Figure 4A:
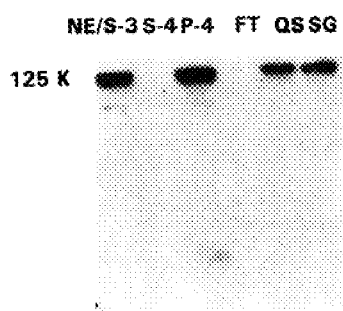
FIGS. 4A–4E: Depicts Western blot analysis of the MDA MB-468 breast cancer cell derived fractions. Thirty micrograms of each protein fraction [PEG NE/S-3, S-4, P-4, Q-Sepharose peak (QS), Q Sepharose flow-through(FT) and sucrose gradient peak (SG)] were resolved on 8% polyacrylamide gels, then transferred to nitrocellulose membrane filters. The membranes were incubated with primary antibodies against (FIG. 4A) DNA polymerase δ.

The DNA Replication Proteins that Copurify with the Breast Cancer Cell DNA Synthesome We performed Western blot analyses and enzyme assays to identify the DNA replication proteins that copurify with the breast cancer cell DNA synthesome during its various stages of purification. As numerous studies have shown that DNA polymerase δ plays an integral role in the in vitro synthesis of SV40 origin containing DNA [8,26,27], we probed the PEG NE/S-3, P-4, S-4, Q-Sepharose peak, Q-Sepharose flow-through and sucrose gradient peak fractions for the presence of the protein. Utilizing a monoclonal antibody prepared against the C-terminal peptide of DNA polymerase δ [28], we found that the protein exclusively co-purified with the replication-competent P-4, Q-Sepharose peak and sucrose gradient peak fractions (FIG. 4A). The enzyme was not detectable in the replication-deficient S-4 and Q-Sepharose flow-through fractions.

Figure 4B:
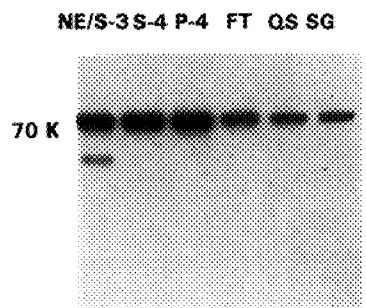
Figure 4C:
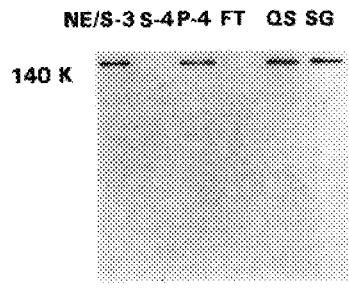

In addition to DNA polymerase δ, we examined the human breast cancer cell fractions for the presence of RF-C [27,29] and DNA primase [27]. Immunoblot analyses, using antibodies that recognize either the 140 kDa subunit of the RF-C protein complex or the 58 kDa subunit of DNA primase, revealed that RF-C and DNA primase resided only in the replication-competent protein fractions (FIGS. 4C and 4E).

Figure 4D:
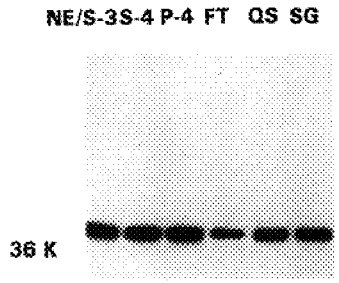
Figure 4E:
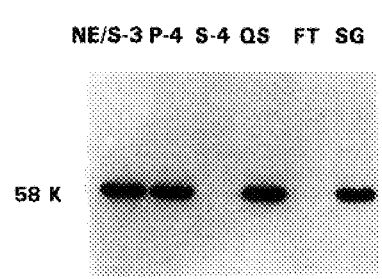

Western blot analysis also shows that the DNA replication protein, PCNA, was present in the replication-competent breast cancer cell fractions, as well as the S-4 and Q-Sepharose flow-through fractions (FIG. 4D). This result suggests that PCNA may not be as tightly associated with the DNA synthesome as compared to DNA polymerases α, δ, RF-C and DNA primase. Furthermore, immunodetection of RP-A [30,31] with a monoclonal antibody to the 70 kDa subunit of the protein, reveals that the polypeptide fractionated with both the replication-competent and -deficient fractions (FIG. 4B). These results suggest that only a fraction of the cellular pools of PCNA and RP-A copurify with the breast cancer cell DNA synthesome.

Figure 5:
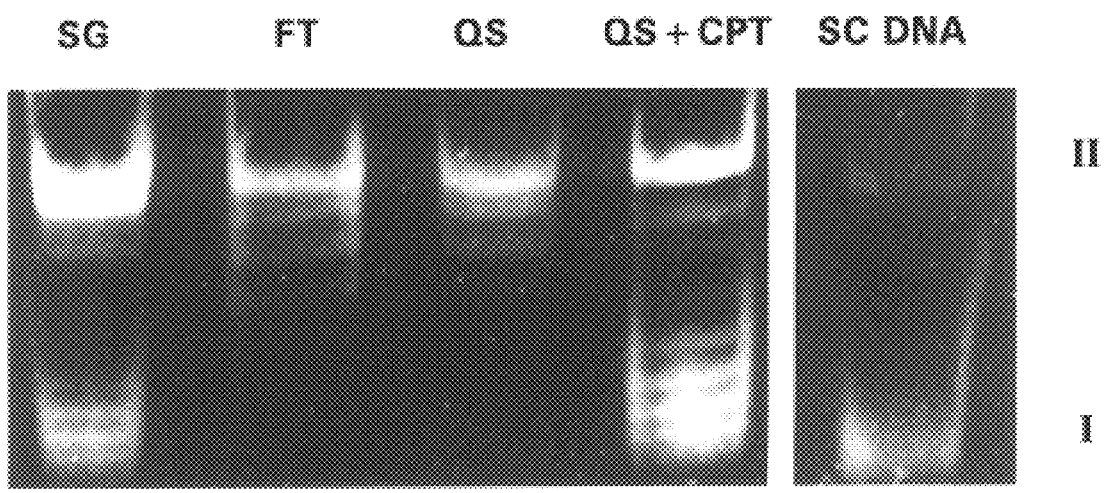
FIG. 5: DNA topoisomerase I activity in the Q-Sepharose peak, Q-Sepharose flow-through and sucrose gradient fractions. Reaction assays containing 8 µg of the Q-Sepharose peak (QS), 8 µg of the Q-Sepharose flow-through (FT), or 20 µg of the sucrose gradient peak (SG) were incubated for 30 minutes at 37° C. with 0.3 µg of pSVO$^+$ plasmid DNA. Reactions were stopped by the addition of 1% agarose gel. After ethidium bromide (0.5 µg/ml) staining of the gels, topoisomers were visualized with an ultraviolet light source. Lanes 1–3 show the conversion of supercoiled, form I DNA to relaxed, open circle form II DNA, by the topoisomerase I activity present in the SG, FT, and QS fractions, respectively. Lane 4 shows the inhibition of QS topoisomerase I activity by 200 µM of camptothecin. Lane 5 shows the position of supercoiled plasmid pSVO$^+$.

Furthermore, we determined whether the breast cancer cell DNA synthesome possesses DNA topoisomerase I activity by assaying several breast cancer fractions for their respective enzymatic activity (Materials and Methods). In FIG. 5, lanes 1–3 show the conversion of supercoiled form I DNA to relaxed, open circular form II DNA by the topoisomerase I activity present in the Q-Sepharose peak, Q-Sepharose flow-through and sucrose gradient peak fractions. Importantly, the relaxation of supercoiled plasmid DNA by the Q-Sepharose peak fraction was inhibited by 200 μM camptothecin (lane 4), a specific inhibitor of DNA topoisomerase I [32]. This indicates that the conversion of supercoiled plasmid DNA to form II DNA was mediated specifically by topoisomerase I.

Figure 6:
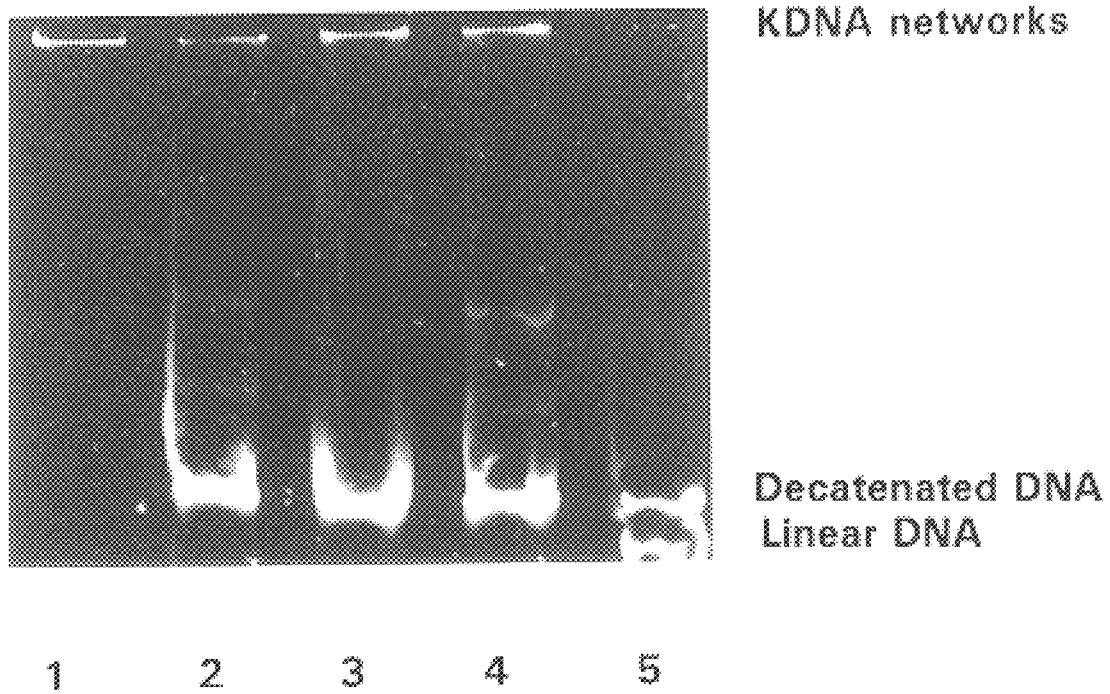
FIG. 6: DNA topoisomerase II activity in the Q-Sepharose peak (QS), Q-Sepharose flow-through (FT) and sucrose gradient (SG) fractions. Decantation reactions were performed in topoisomerase II buffer (TopoGen) with 0.15 µg of KDNA and 10 µg of the respective protein fraction. Lane 1 shows the position of KDNA networks after incubation with QS in a buffer lacking ATP. Lanes 2–4 show the relaxation of KDNA to nicked, open circular DNA by the topoisomerase II activity present in the QS, the FT, and the SG fractions, respectively. Lane 5 shows the positions of the decanted KDNA markers: nicked, open circular (top), linear (bottom). All reactions were were stopped by the addition of a buffer containing 1 % SDS. Reactions were loaded directly onto a 1% agarose gel containing 0.5 µg ethidium bromide. After electrophoresis, DNA products were visualized with a UV light source.

As with PCNA, RP-A and DNA topoisomerase I, only a fraction of the total cellular pool of DNA topoisomerase II co-purifies with the breast cancer cell DNA synthesome. We assayed the Q-Sepharose peak, Q-Sepharose flow-through and sucrose gradient peak fractions for DNA topoisomerase II activity. The decatenation of interlocked aggregates of *Crithidia fasisculata* kinetoplast DNA to monomeric, open circular DNA by the topoisomerase II enzyme present in all three fractions is shown in. FIG. 6 (lanes 2–4). In addition, we determined that the Q-Sepharose peak, flow-through and sucrose gradient peak fractions were devoid of nuclease contamination because they did not support the relaxation of kinetoplast DNA to the linear DNA fragments (FIG. 6). Moreover, as DNA topoisomerase II requires ATP for catalytic activity, incubation of the Q-Sepharose peak with a reaction buffer lacking ATP did not support the relaxation of kinetoplast DNA (FIG. 6, lane 1).

Isolation of the DNA synthesome from Breast Tumor Tissue

In order to verify that the DNA synthesome could be isolated from breast cancer tissue as well as breast cancer cells, we subjected biopsied human breast tumor tissue to a modified version of the purification scheme depicted in FIG. 1 (Materials and Methods). The alterations to the purification protocol were made to facilitate the isolation of the DNA synthesome from small quantities of breast tumor tissue. We collected and assayed the NE/S-3, S-4 and P-4 fractions for DNA polymerase α and large T-antigen dependent SV40 DNA replication activities. Table 3 shows that the majority of both activities partitioned exclusively with the sedimentable P-4 fraction after discontinuous gradient centrifugation of the NE/S-3 fraction.

TABLE 3

DNA polymerase α and in vitro DNA replication activities of the DNA synthesome from human breast tumor tissue.

| Fraction | NE/S-3 | S-4 | P-4 |
|---|---|---|---|
| DNA polymerase α* | 27.8 | 1.7 | 37.5 |
| DNA Replication +T[#] | 29.5 | 1.8 | 122.9 |
| DNA Replication −T[#] | 5.74 | 0.5 | 12.1 |

*DNA polymerase α activity with activated calf thymus DNA templates was assayed according to published procedures [21, 22] and as described in the Materials and Methods. One unit of DNA polymerase activity is equivalent to $1 \times 10^{-10}$ mol of [$^3$H]-TMP incorporated into DNA per hour at 35° C. These values represent the average of two independent experiments.
[#]In vitro SV40 DNA replication assays were performed as described in the Materials and Methods. One unit of replication activity equals the incorporation of 1 pmol [$^{32}$P]-dCMP into SV40 origin containing DNA. These values represent the average of two independent experiments.

We further purified the DNA synthesome that was isolated from the human breast tumor tissue, using ion exchange chromatography (Materials and Methods). We collected and assayed the column fractions for both DNA polymerase α and in vitro SV40 DNA replication activities. A peak of DNA polymerase α activity (fractions 2,3) was found to elute from the column in the presence of 1M KCl (Table 4). In contrast, only a minor amount of DNA polymerase α activity was found in the column flow-through fraction (Table 4). We also tested the fractions containing the peak polymerase α activity (fractions 2,3) as well as the column flow-through for in vitro SV40 DNA replication activity. Only fractions 2 and 3 supported SV40 DNA replication; the column flow-through did not contain DNA replication activity (data not shown).

TABLE 4

DNA polymerase α activity of the column purified DNA synthesome from human breast cancer tissue.

| Fraction | Peak | Flow-through |
|---|---|---|
| DNA polymerase α* | 77.3 | 1.3 |

*DNA polymerase α activity with activated calf thymus DNA templates was assayed according to published procedures [21, 22] and as described in the Materials and Methods. One unit of DNA polymerase activity is equivalent to $1 \times 10^{-10}$ mol of [$^3$H]-TMP incorporated into DNA per hour at 35° C. Fractions 2 and 3 constitute the peak of DNA polymerase α activity. These values represent the average of two independent experiments.

We also fractionated breast cancer tissue-derived from a xenograft nude mouse model [17]. Homogenous breast tumors were surgically excised from nude mice subcutaneously injected with MCF-7 breast cancer cells. Using the modified purification protocol, it was found that most of the DNA polymerase α and DNA replication activities resided with the sedimentable P-4 fraction following discontinuous gradient centrifigation of the NE/S-3 fraction (Table 5). These results suggest that the DNA synthesome exists as a functional complex within human breast cancer cells in vivo.

TABLE 5

DNA polymerase α and in vitro SV40 DNA replication activities of the DNA synthesome from nude mouse tumor tissue.

| Fraction | NE/S-3 | S-4 | P-4 |
|---|---|---|---|
| DNA polymerase α* | 40.6 | 2.0 | 123.2 |
| DNA Replication +T# | 57.2 | 11.2 | 158.7 |
| DNA Replication −T# | 5.5 | 4.1 | 9.6 |

*DNA polymerase α activity with activated calf thymus DNA templates was assayed according to published procedures [21, 22] and as described in the Materials and Methods. One unit of DNA polymerase activity is equivalent to $1 \times 10^{-10}$ mol of [$^3$H]-TMP incorporated into DNA per hour at 35° C. These values represent the average of two independent experiments.
In vitro SV40 DNA replication assays were performed as described in the Materials and Methods. One unit of replication activity equals the incorporation of 1 pmol of [$^{32}$P]-dCMP into SV40 origin containing DNA. These values represent the average of two independent experiments.

DNA Polymerase ε Copurifies with the Breast Cancer Cell DNA Synthesome

Figure 7:
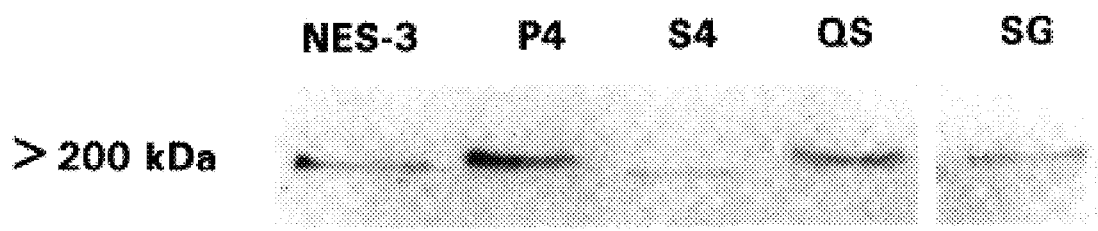
FIG. 7: Immunoblot analysis for the presence of DNA polymerase ε in the MDA MB-468 breast cancer cell derived fraction. 50 µg of each protein fraction [PEG NE/S-3, S-4, P-4, Q-Sepharose peak (QS), and sucrose gradient peak (SG)] were resolved on 8% polyacrylamide gels, then transferred to nitrocellulose membrane filters. The membranes were incubated with primary antibodies against human DNA polymerase ε. Following incubation with the anti-mouse secondary antibody conjugated to horseradish peroxidase, the immobilized protein was detected using a light enhanced chemi-luminescence system (Amersham).

Several lines of evidence support a role for DNA polymerase ε in cellular DNA replication. First, DNA polymerase ε is more abundant in proliferating tissues than in non-proliferating tissues [33]. Second, when quiescent human fibroblast cells are stimulated to proliferate, the mRNA levels of DNA polymerase ε, like those of polymerase α, dramatically increase just prior to S-phase [33]. Third, when the gene encoding the yeast homologue of DNA polymerase ε is mutated, the yeast cells fail to proliferate; suggesting a critical role for this polymerase in cell proliferation [34]. In order to determine whether DNA polymerase ε copurifies with the breast cancer cell DNA synthesome, we probed the MDA MB-468 derived protein fractions with an antibody that recognizes the >200 kDa polypeptide. Immunoblot analysis reveals that DNA polymerase ε was present in the replication-competent P-4, Q-Sepharose peak and sucrose gradient peak fractions (FIG. 7). Only a minor amount of DNA polymerase ε was present in the replication-deficient S-4 fraction (FIG. 7), while none was detected in the Q-Sepharose flow-through (data not shown).

DNA Replication Fidelity of the Breast Cancer Cell DNA Synthesome

The fidelity of DNA synthesis is mediated in part by the proof-reading capacity of the intrinsic 3'-5' exonuclease activity of DNA polymerase δ [25]. We employed a forward mutagenesis assay to measure the fidelity of the in vitro DNA synthesis process carried out by the breast cancer cell DNA synthesome (Materials and Methods) [35]. In this assay we utilized the DNA synthesome isolated from MDA MB-468 breast cancer cells and human breast tumor tissue to replicate plasmid DNA containing the SV40 origin of replication and the lac-Zα gene. The results of the fidelity assay were quantitated using the blue/white selection protocol described in the Materials and Methods [25]. These results were compared to the replication fidelity of the DNA synthesome isolated from non-malignant Hs587Bst breast cells. We determined that the DNA synthesome from MDA MB-468 cells possessed a replication fidelity approximately 6 fold lower than that of the synthesome from Hs587Bst cells (Table 6). Similarly, the DNA synthesome purified from human breast tumor tissue possessed an approximately 5-fold lower DNA replication fidelity than the Hs587Bst synthesome (Table 6). These differences in replication fidelity between the malignant and normal breast cell DNA synthesome suggest that transformation to the malignant phenotype alters the process by which the synthesome from normal cells replicates DNA.

TABLE 6

DNA replication fidelity of the breast cell DNA synthesome: Blue/White selection assay.

| Origin of Synthesome | % mutants (ave. per $10^4$ colonies) |
|---|---|
| MDA-MB 468 cell line | 1.20% ± 0.2% |
| Human breast cancer tissue | 0.93% ± 0.3% |
| Hs578 Bst (non-malignant) | 0.19% ± 0.08% |

An in vitro DNA replication fidelity assay [37] was used to measure the fidelity with which the synthesome from MDA MB 468 cells, human breast tumor tissue and Hs587Bst cells replicates plasmid DNA. The replicated plasmid, containing the bacterial lac-Z gene, was Dpn I digested and electroporated into *E. coli*, which were then plated onto LB agar containing the chromogenic substrates, X-gal and IPTG. Transformed bacteria expressing a non-mutated lac-Z gene (encodes the B-galactosidase enzyme) formed blue colonies on the plate, while bacteria containing DNA with mutations in the lac-Z gene formed white colonies. Mutations occurring in locations other than the lac-Z gene on the pBK-CMV plasmid are not detected by this forward mutagenesis assay. Consequently, the reported percentages of white colonies provide a minimum estimate of the actual number of mutations occurring in DNA synthesome mediated DNA replication. The percentage of mutant colonies expressed for each breast cell DNA synthesome is the average number taken from 3 separate assays of $10^4$ transformed colonies each.

Discussion

In this report, we have described for the first time the purification of a multiprotein DNA replication complex isolated from human breast cancer cells and breast tumor tissues. The integrity of the breast cancer cell DNA synthesome was maintained after treatment with high salt, polyethylene glycol precipitation, anion-exchange chromatography and sucrose gradient sedimentation. These results suggest that the co-purification of the synthesome's proteins with one another is independent of non-specific interactions with other cellular macromolecules. In addition, upon velocity sedimentation analysis of the breast cancer cell DNA synthesome, both the DNA polymerase α and DNA replication activities co-migrated in the sucrose gradient with a coefficient of 18S. This 18S sedimentation coefficient is comparable to that obtained for the HeLa cell DNA synthesome [13,14].

Our data show that the DNA polymerase α and DNA replication activities of the synthesome isolated from breast cancer cells and breast tumor tissues, was enriched by the successive steps of the purification process. Furthermore, the P-4 as well as the Q-Sepharose peak fractions from the breast cancer cells and tissues possessed comparable levels of in vitro SV40 DNA replication activity. Overall, the isolation of the DNA synthesome as a fully functional complex from human and nude mouse xenograft breast tumor tissues, strongly suggests that the synthesome mediates DNA replication in vivo.

We have identified several of the key DNA replication proteins comprising the breast cancer cell DNA synthesome utilizing immunoblot analyses and enzymatic assays; these proteins include: DNA polymerase δ, PCNA, DNA polymerase α, DNA primase, RF-C, RP-A, DNA topoisomerases I, II, and DNA polymerase ε. All of these polypeptides, excluding DNA polymerase ε, have been shown to be required for the faithful replication of SV40 DNA in vitro [8,9,10]. Moreover, the functions that each of these proteins performs during DNA replication have been determined by utilizing the SV40 system. Recent studies demonstrate that DNA polymerase α-primase synthesizes RNA-DNA primers required for the initiation of leading strand and Okazaki fragment synthesis [36,37]. On the other hand, DNA polymerase δ conducts the replication of the leading strand during DNA chain elongation [36,38]. According to a current model for eukaryotic DNA replication, the activities of both DNA polymerases α and δ are coordinated in part by RF-C, which serves as a connector or hinge between the proteins; [27]. Additionally, PCNA—an accessory factor for polymerase δ—may participate in the coordination of leading and lagging strand synthesis by functioning as part of a molecular switch from the initiation to the elongation phase of DNA replication [38,39]. The co-purification of DNA polymerases α, δ, DNA primase, PCNA and RF-C with the breast cancer cell DNA synthesome indicates that the synthesome may act as a coordinated dipolymerase replication complex.

RP-A functions during SV40 DNA synthesis to stabalize newly formed single-stranded regions created in replicating DNA by the helicase activity of the large T-antigen [40]. Topoisomerase I, also a component of the breast cancer cell DNA synthesome, relaxes positive DNA supercoils as they accumulate ahead of the replication fork [41]. Such an action is necessary for translocation of the replication machinery along template DNA during DNA synthesis. In addition to topoisomerase I, topoisomerase II can carry out the unwinding activity required for the progression of the replication fork during SV40 DNA synthesis [41]. Furthermore, studies in which intact cells were incubated with topoisomerase II inhibitors demonstrate that the topoisomerase II is necessary for the decatenation of newly replicated daughter DNA molecules [42] following DNA synthesis. Presumably the enzyme functions in these roles as a component of the DNA synthesome. We are presently characterizing the breast tumor tissue-derived synthesome with respect to its protein components. Although not yet identified as components of the breast cancer cell DNA synthesome, DNA helicase and DNA ligase I were found to copurify with the synthesome isolated from HeLa and FM3A cells [14,15]. Both of these enzymes have been shown to be required for eukaryotic DNA replication in vivo [43,44]. Presumably, all of the proteins comprising the breast cancer cell DNA synthesome copurify with the tumor tissue-derived synthesome, as it is fully capable of supporting SV40 DNA replication in vitro.

In order to preserve the integrity of the information contained in DNA, normal mammalian cells must replicate their DNA with an error frequency as low as $10^{-10}$ [33]. Such a high fidelity for DNA replication must be maintained by the DNA synthesis and DNA repair systems functioning within the cell. We utilized a forward mutagenesis assay [25] to examine the fidelity with which the breast cancer cell and human breast tumor tissue DNA synthesome replicates plasmid DNA containing the lac-Zα gene. This assay detects point mutations occurring within the lac-Zα gene as well as frame-shift mutations occurring in other positions on the plasmid. We found a 5–6 fold decrease in the replication fidelities of the DNA synthesome isolated from malignant breast cells and tissue compared to that of the normal breast cell DNA synthesome (Table 6). Our results are consistent with the observation that mammary cancer cells accumulate extensive genetic damage [45,46]. The significant difference in the replication fidelities between the malignant and normal breast cell DNA synthesome suggests that transformation alters the process by which the latter replicates and/or participates in the repair of DNA. Indeed, it has been demonstrated that specific DNA replication proteins are targets for molecular modification during cellular transformation [4]. For example, DNA polymerases α and ε purified from Novikoff hepatoma cells have altered physicochemical and catalytic properties compared to the respective polymerases isolated from normal liver cells [4]. During DNA synthesis, these altered molecular and catalytic properties may contribute to a decreased specificity for nucleotide selection by the polymerases, which in turn leads to an increased mutation rate. Importantly, we have determined by two-dimensional polyacrylamide gel electrophoresis that significant physical differences exist between the protein components of the DNA synthesome purified from malignant and normal breast cells.[8] We are currently conducting experiments to determine the precise molecular changes that occur to the components of the breast cell DNA synthesome during transformation. We fully expect these studies to advance our understanding of how DNA replication fidelity is reduced in breast cancer cells.

Figure 8:
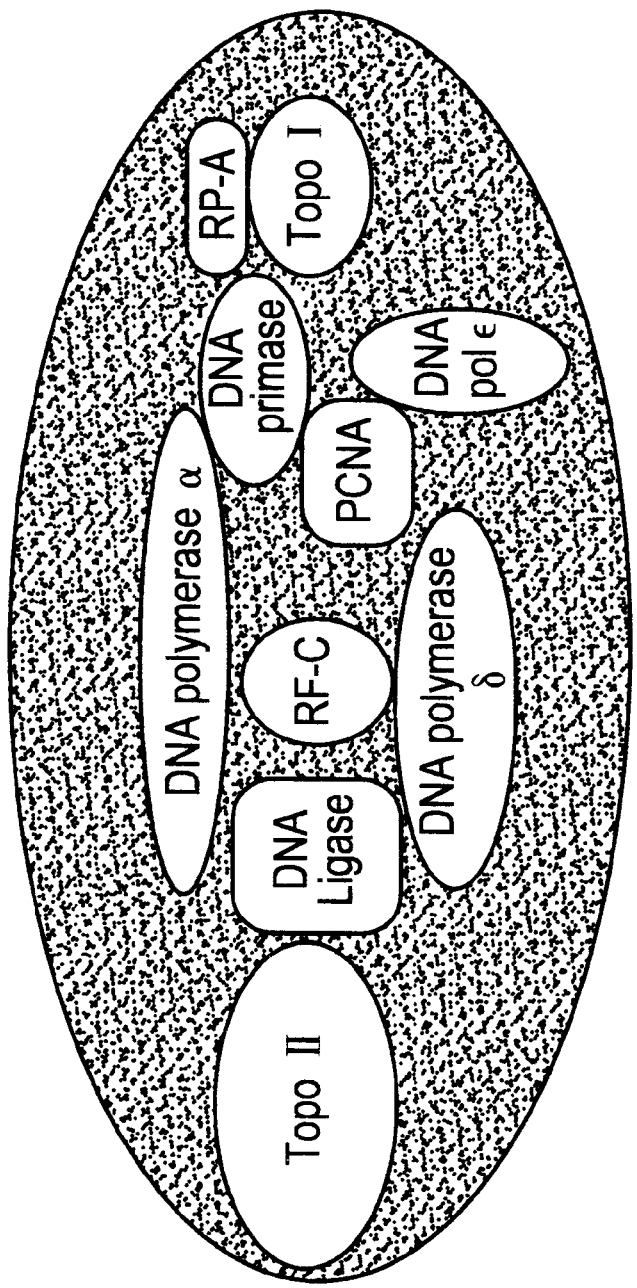
FIG. 8: Model for the human breast cell DNA synthesome.

We previously described a model for the organization of the proteins comprising the DNA synthesome isolated from mouse mammary carcinoma cells and HeLa cells [14,15]. We can now extend this model to include the breast cancer cell DNA synthesome, based on the fractionation and column chromatographic profiles of its protein components (FIG. 8). As DNA polymerases α, δ, ε, DNA primase and RF-C were observed to copurify primarily with the replication-competent DNA synthesome, we propose that these proteins form the core of the DNA synthesome. The "tight" association of DNA polymerase ε with the DNA synthesome suggests that the protein may play a role in mammalian cell DNA replication in vivo. It has been postulated that DNA polymerase ε links the replication machinery with the S-phase checkpoint by acting as a sensor that coordinates transcriptional responses to DNA damage in yeast [47]. Such a role for the protein may exist in mammalian cells as well. In addition, we have included DNA ligase I as a member of the tightly associated components of the complex as it was observed to exclusively copurify with the DNA synthesome from FM3A and HeLa cells [14,15].

Unlike the other components, PCNA, RP-A and topoisomerases I and II were observed to co-fractionate and co-elute, following column chromatography, with those fractions containing the breast cancer cell DNA synthesome as well as with fractions lacking DNA replication activity. These results suggest that only a fraction of the cellular pools of PCNA, RP-A, and topoisomerases I, II, copurify with the DNA synthesome. This is consistent with the recognition that these proteins have additional roles in mediating cellular functions such as transcription, recombination and repair. During the initial stages of SV40 DNA replication, both topoisomerase I and RP-A facilitate the melting of SV40 DNA [48]. Therefore, we propose that both of these proteins constitute the "initiation" components of the breast cancer cell DNA synthesome. We are currently performing co-immunoprecipitation studies to determine the exact physical interactions of the synthesome's proteins with each other. Their physical association depicted in FIG. 8 is consistent with data from our laboratory as well as with several reports on SV40 and eukaryotic DNA replication [7,8,27,38].

In this report, we have isolated and described a multiprotein complex for DNA replication from breast cancer cells and breast tumor tissues. The isolation of a fully functional DNA synthesome from tumor tissues strongly suggests that the synthesome mediates breast cancer cell DNA replication in vivo. Furthermore, we have established that the human breast cancer cell and tumor tissue-derived DNA synthesome possess a lower fidelity for DNA replication than the synthesome purified from non-malignant breast cells. Breast cancer cells possess high rates of DNA synthesis and an accumulation of genetic damage [2, 45,46]. Understanding the process of DNA replication, as it occurs in breast cancer cells in vivo, will greatly facilitate the development of improved anti-breast cancer agents. We fully expect that the complete characterization of the breast cancer cell DNA synthesome will further our understanding of aberrant breast cell DNA replication as well as contribute to the development of these improved therapies.

The examples discussed herein are provided for illustrative purposes only, and are in no way intended to limit the scope of the present invention.

While the invention has been described in detail, and with reference to specific embodiments thereof, it will be apparent to one with ordinary skill in the art that various changes and modifications can be made therein without departing from the spirit and scope thereof.

All references cited herein are incorporated by reference in their entirety.

REFERENCES

1. American Cancer Society, Basic Data, 1996.
2. Keshgegian, A. and Cnaan, A. (1995) Proliferation markers in breast carcinoma: mitotic figure count, S-phase fraction, proliferating cell nuclear antigen, Ki-67 and MIB-1. Anat Path 104:42–49.
3. Loeb, L. (1991) Mutator phenotype may be required for multistage carcinogenesis. Cancer Res. 51:3075–3079.
4. Popanda, O., Fox, G. and Thielmann, H. W. (1995) DNA polymerases α,δ and ε of Novikoff hepatoma cells differ from those of normal rat liver in physicochemical and catalytic properties. J. Mol. Med. 73:259–268.
5. Kelly, T J (1988) SV40 DNA replication. JBC 263:17889–17892.
6. Challberg, M. and Kelly, T. (1989) Animal virus DNA replication. Annu Rev Biochem 58:671–717.
7. Stillman, B. (1989) Initiation of eukaryotic DNA replication in vitro. Annu Rev Cell Bio 5:107–245.
8. Hurwitz, J., Dean, F. B., Kwong, A. D., Lee, S. H. (1990) The in vitro replication of DNA containing the SV40 origin. JBC 265:18043–18046.
9. Malkas, L. H., Hickey, R. J. and Baril, E. F. (1990a) Multienzyme complexes for DNA synthesis in eukaryotes: P-4 revisited. In: Strauss, P. R. and Wilson, S. H. (eds.) "The Eukaryotic Nucleus: Molecular Biochemistry and Macromolecular Assemblies." New Jersey, The Telford Press, pp. 45–68.
10. Stillman, B., Bell, S. P., Dutta, A., Marahrens, Y. (1992): In "Regulation of the Eukaryotic Cell Cycle" (Ciba Foundation Symposium 170) Chichester: John Wiley and Sons, pp 147–156.
11. Matthews, C. K. and Slabaugh, M. B. (1986) Eukaryotic DNA metabolism: Are deoxynucleotides channeled to replication sites? Exp Cell Res 162:285–295.
12. Reddy, G. and Fager, R. (1993) Replitase: A complex integrating dNTP synthesis and DNA replication. Crit Rev Euk Gene Exp 3:255–277.
13. Malkas, L. H., Hickey, R. J., Li, C. J., Pedersen, N. and Baril, E. F. (1990b) A 21S enzyme complex from HeLa cells that functions in simian virus 40 (SV40) DNA replication in vitro. Biochem. 29: 6362–6374.
14. Applegren, N., Hickey, R. J., Kleinschmidt, A. M., Zhou, Q., Coll, J., Wills, P., Swaby, R., Wei, Y., Quan, J. Y., Lee, M. and Malkas, L. H. (1995) Further characterization of the human cell multiprotein DNA replication complex (MRC). J. Cell. Biochem. (in press).
15. Wu, Y., Hickey, R. J., Lawlor, K., Wills, P., Yu, F., Ozer, H., Starr, R., Quan, J. Y., Lee, M. and Malkas, L. H. (1994) A 17S multiprotein form of murine cell DNA polymerase mediates polyomavirus DNA replication in vitro. J. Cell. Biochem. 54: 32–46.
16. Tom, T., Hickey, R. J. and Malkas, L H. (1995) Identification of multiprotein complexes containing DNA replication factors by native immunoblotting of HeLa cell protein preparations with T-antigen dependent SV40 DNA replication activity. J Cell Biochem (in press).
17. Yue, W., Zhou, D., Chen, S. and Brodie, A. (1994) A nude mouse model for postmenopausal breast cancer using MCF-7 cells transfected with the human aromatase gene. Cancer Res 54:5092–5095.
18. Simanis, V. and Lane, D. P. (1985) An immunoaffinity purification procedure for SV40 large T-antigen. Virology 144: 88–100.
19. Stillman, B., Gerard, R. D., Guggenheimer, R. A. and Gluzman, Y. (1985) T-antigen and template requirements for SV40 DNA replication in vitro. EMBO J. 4: 2933–2939.
20. Sambrook, J., Fritsch, E., and Maniatis, T. (1989) In: Molecular Cloning: A Laboratory Manual, 2nd edition, Cold Spring Harbor Laboratory Press, Cold Spring Harbor, N.Y.
21. LaMothe, P., Baril, B., Chi, A., Lee, L. and Baril B. (1981) Accessory proteins for DNA polymerase α activity with single-strand DNA templates. PNAS 78:4723–4727.
22. Vishwanatha J. K., Yamaguchi, M., DePamphilis, M. L. and Baril, E. F. (1986) Selection of template initiation sites and the lengths of RNA primers synthesized by DNA primase are strongly affected by its organization in a multiprotein DNA polymerase α complex. Nuc Acid Res 14:7305–7323.
23. Hickey, R. J., Malkas, L. H., Pedersen, N., Li, C. and Baril, E. F. (1988) Multienzyme complex for DNA replication in HeLa cells. Moses, R. and Summers, W. (eds.) In: DNA Replication and Mutagenesis, Amer. Soc. Microbiol. Public., Washington D.C., pp. 41–54.
24. Laemmli U. K. (1970) Cleavage of structural proteins during the assembly of the head of bacteriophage T4. Nature 227:680–685.
25. Roberts, J. D. and Kunkel, T. A. (1988) The fidelity of a human cell DNA replication complex. PNAS 85:7064–7068.
26. Prelich, G., Tan, C. K., Mikostura, M., Matthews, B., So, A. G., Downey, K. M. and Stillman, B. (1987) Functional identity of proliferating cell nuclear antigen and a DNA polymerase δ auxiliary protein. Nature (London) 326:517–520.
27. Tsurimoto, T. and Stillman, B. (1991) Replication factors required for SV40 DNA replication in vitro. JBC 266:1961–1968.
28. Lee, M Y W T, Tan C. K., Downey, K. M. and So, A. G. (1984) Further studies on calf thymus DNA polymerase δ purified to homogeneity by a new procedure. Biochem 23:1906–1913.
29. Lee S. H., Kwong, A. D., Pan, Z. Q. and Hurwitz, J. (1991) Studies on the activator-1 protein complex, an accessory factor for proliferating cell nuclear antigen-dependent DNA polymerase delta JBC 266:594–602.
30. Wobbe, R. C., Dean, F., Weissbach, L. and Hurwitz, J. (1985) In vitro replication of duplex circular DNA containing the simian virus 40 DNA origin site. PNAS 82: 5710–5714.
31. Fairman, M. P. and Stillman, B. (1988) Cellular factors required for multiple stages of SV40 DNA replication in vitro. EMBO J 7:1211–1218.
32. Hsiang, Y. H. and Liu, L. F. (1988) Identification of mammalian DNA topoisomerase I as an intracellular target of the anticancer drug camptothecin. Cancer Res. 48: 1722–1726.
33. Tuusa, J., Uitto, L. and Syvaoja, J. (1995) Human DNA polymerase $\epsilon$ is expressed during cell proliferation in a manner characteristic of replicative DNA polymerases. Nuc Acid Res 23: 2178–2183.
34. Morrison, A., Araki, H., Clark, A. B., Hamatake, R. B. and Sugino, A. (1990) A third essential DNA polymerase in S. cerevisiae. Cell 62: 1143–1151.
35. Roberts, J. D., Thomas, D. C. and Kunkel, T. A. (1991) Exonucleolytic proofreading of leading and lagging strand DNA replication errors. PNAS 88:3465–3469.
36. Stillman, B. (1994) Smart machines at the DNA replication fork. Cell 78: 725–728.
37. Denis, D. and Bullock, P. (1993) Primer-DNA formation during simian virus 40 DNA replication in vitro. Mol. and Cell Bio. 13:2882–2890.
38. Waga, S. and Stillman, B. (1994) Anatomy of a DNA replication fork revealed by reconstitution of SV40 DNA replication in vitro. Nature 369:207–212.
39. Prelich, G. and Stillman, B. (1988) Coordinated leading and lagging strand synthesis during SV40 DNA replication in vitro requires PCNA. Cell 53:117–126.
40. Wobbe, C. R., Dean, F., Weissbach, L. and Hurwitz, J. (1985) In vitro replication of duplex circular DNA containing the simian virus 40 DNA origin site. PNAS 82:5710–5714.
41. Yang, L., Wold, M. S., Li, J. J., Kelly, T. J. and Liu, L. F. (1987) Roles of DNA topoisomerases in simian virus 40 DNA replication. PNAS 84:940–954.
42. Snapka, R. M. (1986) Topoisomerase inhibitors can selectively interfere with different stages of simian virus 40 DNA replication. Mol. Cell. Bio. 6:4221–4227.
43. Budd, M. E., Choe, W. C. and Campbell, A. L. (1995) DNA2 encodes a DNA helicase essential for replication of eukaryotic chromosomes. JBC 270: 260766–9.
44. Petrini, J. H., Xiao, Y. and Weaver, D. T. (1995) DNA ligase I mediates essential functions in mammalian cells. Mol. Cell. Bio. 15:4303–4308.
45. Thorgeirsson, S. S. (1993) Endogenous DNA damage and breast cancer. Cancer 71:2897–2899.
46. Nutter, L. M., Wu, Y. Y., Ngo, E. O., Sierra, E. E., Gutierrez, P. L. and Abul-Hajj, Y. J. (1994) An o-quinone form of estrogen produces free radicals in human breast cancer cells: correlation with DNA damage. Chem. Res. Tox. 7:23–28.
47. Navas, T. A., Zhou, Z. and Elledge, S. J. (1995) DNA polymerase $\epsilon$ links the DNA replication machinery to the S phase checkpoint. Cell 80:29–39.
48. Boroweic, J. A., Dean, F. B., Bullock, P. A. and Hurwitz, J. (1990) Binding and unwinding: How T-antigen engages the SV40 origin of DNA replication. Cell 60:181–184.

Acknowledgements

We are grateful to Yuetong Wei and QiQi Zhou for their technical expertise.

We claim:

1. A method for detecting the presence of malignant tissue or malignant cells comprising the steps of:
   (A) obtaining a multi-protein DNA replication complex capable of supporting DNA replication by the method comprising:
      (1) homogenizing a sample comprising tissue or cells to obtain a homogenate;
      (2) separating the homogenate obtained in step (1) into a nuclear pellet and a cytosolic extract;
      (3) extracting nuclei from said nuclear pellet obtained in step (2) to obtain a nuclear extract;
      (4) subjecting the cytosolic extract obtained in step (2) to repeated differential centrifugation to obtain a post-microsomal supernatant;
      (5) combining said nuclear extract obtained in step (3) with said post-microsomal supernatant obtained in step (4) in the presence of polyethylene glycol (PEG) to obtain a suspension;
      (6) subjecting the suspension obtained in step (5) to centrifugation to obtain a PEG-supernatant;
      (7) subjecting the PEG-supernatant obtained in step (6) to dialysis to obtain a dialyzate;
      (8) subjecting the dialyzate obtained in step (7) to centrifugation to clarify said dialyzate and obtain a supernatant solution;
      (9) subjecting the supernatant solution obtained in step (8) to sucrose centrifugation and collecting sucrose interface fractions resulting from said centrifugation;
      (10) subjecting the sucrose interface fractions obtained in step (9) to dialysis to obtain dialyzed fractions; and
      (11) collecting fractions containing DNA replication activity,
         wherein said sample in said method comprises tissue or cells suspected of being malignant, so as to obtain a test complex;
   (B) obtaining a multi-protein DNA replication complex capable of supporting DNA replication by the method comprising steps (1)–(11) above, except
      wherein said sample in said method comprises normal tissue or cells, so as to obtain a control complex;
   (C) contacting, in vitro, said test complex obtained in step (A) with a DNA template comprising an origin of replication recognized by said test complex under conditions to achieve DNA synthesis;
   (D) contacting, in vitro, said control complex obtained in step (B) with a DNA template comprising an origin of replication recognized by said control complex under conditions to achieve DNA synthesis; and
   (E) comparing the frequency of mutation occurrence in the presence of said test complex with the frequency of DNA mutation occurrence in the presence of said control complex so as to detect the presence of malignant tissue or malignant cells.

2. The method of claim 1, wherein the method further comprises the step of:
   (12) subjecting the dialyzed fractions of step (11) to anion-exchange chromatography and collecting fractions containing DNA replication activity.

3. The method of claim 1, wherein said sample comprises tissue.

4. The method of claim 3, wherein said tissue suspected of being malignant is breast tumor tissue.

5. The method of claim 1, wherein said sample comprises cells.

6.. The method of claim 5, wherein said cells suspected of being malignant are carcinoma cells.

7. The method of claim 6, wherein said carcinoma cells are selected from the group consisting of human cervical carcinoma cells, mouse mammary carcinoma cells and breast carcinoma cells.

8. The method of claim 7, wherein said human cervical carcinoma cells are HeLa cells and said mouse mammary carcinoma cells are FM3A cells.

9. The method of claim 5, wherein said cells suspected of being malignant are human leukemia cells.

10. The method of claim 5, wherein said cells suspected of being malignant are human breast cells.

11. The method of claim 10, wherein said human breast cells are selected from the group consisting of MDA MB-468 cells, MCF-7 cells and Hs587Bst cells.

12. The method of claim 1, wherein said DNA replication activity is SV40 DNA replication activity.

13. A method for detecting the presence of malignant tissue or malignant cells comprising the steps of:
    (A) obtaining a multi-protein DNA replication complex capable of supporting DNA replication from a sample of tissue or cells suspected of being malignant, so as to obtain a test complex:
    (B) obtaining a multi-protein DNA replication complex capable of supporting DNA replication from a sample of normal tissue or cells, so as to obtain a control complex;
    (C) contacting, in vitro, said test comples obtained in step (A) with a DNA template comprising an origin of replication recognized by said test complex under conditions to achieve DNA synthesis;
    (D) contacting, in vitro, said control complex obtained in step (B) with a DNA template comprising an origin of replication recognized by said control complex under conditions to achieve DNA synthesis; and
    (E) comparing the frequency of mutation occurrence in the presence of said test complex with the frequency of DNA mutation occurrence in the presence of said control complex so as to detect the presence of malignant tissue or malignant cells.

14. The method of claim 13, wherein said sample comprises tissue.

15. The method of claim 14, wherein said tissue suspected of being malignant is breast tumor tissue.

16. The method of claim 13, wherein said sample comprises cells.

17. The method of claim 16, wherein said cells suspected of being malignant are carcinoma cells.

18. The method of claim 17, wherein said carcinoma cells are selected from the group consisting of human cervical carcinoma cells, mouse mammary carcinoma cells and breast carcinoma cells.

19. The method of claim 18, wherein said human cervical carcinoma cells are HeLa cells and said mouse mammary carcinoma cells are FM3A cells.

20. The method of claim 16, wherein said cells suspected of being malignant are human leukemia cells.

21. The method of claim 16, wherein said cells suspected of being malignant are human breast cells.

22. The method of claim 21, wherein said human breast cells are selected from the group consisting of MDA MB-468 cells, MCF-7 cells and Hs587Bst cells.

23. The method of claim 13, wherein said multi-protein DNA replication complex has SV40 DNA replication activity.

* * * * *

UNITED STATES PATENT AND TRADEMARK OFFICE
CERTIFICATE OF CORRECTION

| | |
|---|---|
| PATENT NO. | : 6,093,543 |
| APPLICATION NO. | : 09/058760 |
| DATED | : July 25, 2000 |
| INVENTOR(S) | : Robert J. Hickey et al. |

It is certified that error appears in the above-identified patent and that said Letters Patent is hereby corrected as shown below:

Title page, item [75] inventors: --add Jennifer W. Sekowski--

Signed and Sealed this

Twenty-seventh Day of March, 2007

JON W. DUDAS
*Director of the United States Patent and Trademark Office*